United States Patent [19]

Allaigre et al.

[11] Patent Number: 5,300,510

[45] Date of Patent: Apr. 5, 1994

[54] SALT OF 6-PIPERIDINO-2,4-DIAMINOPYRIMIDINE 3-OXIDE AND ACETURIC ACID, ITS PREPARATION AND ITS DERMATO-COSMETOLOGICAL APPLICATION

[75] Inventors: Jean-Pierre Allaigre, Ezanville; Jacques Desbois, Persan, both of France

[73] Assignee: Norchim, Saint Leu D'Esserent

[21] Appl. No.: 11,122

[22] Filed: Jan. 29, 1993

Related U.S. Application Data

[63] Continuation of Ser. No. 779,152, Oct. 21, 1991, abandoned, which is a continuation of Ser. No. 410,660, Sep. 21, 1989, abandoned.

[30] Foreign Application Priority Data

Sep. 23, 1988 [FR] France .................. 88 12442

[51] Int. Cl.$^5$ .................. A61K 31/505; C07D 401/04
[52] U.S. Cl. .................................... 514/272; 514/880; 544/324
[58] Field of Search ............. 514/272, 880; 544/324

[56] References Cited

U.S. PATENT DOCUMENTS 4,139,619 2/1979 Chidsey, III ............ 544/324

FOREIGN PATENT DOCUMENTS 2132726 11/1972 France .
2590897 6/1987 France .
2175901A 12/1986 United Kingdom .
2183632 6/1987 United Kingdom .

OTHER PUBLICATIONS

The Merck Index, 10 Ed.; 75 and 6069 (1983).

*Primary Examiner*—Mary C. Lee
*Assistant Examiner*—Michael G. Ambrose
*Attorney, Agent, or Firm*—Dressler, Goldsmith, Shore & Milnamow, Ltd.

[57] ABSTRACT

The present invention relates to minoxidil aceturate corresponding to the formula I

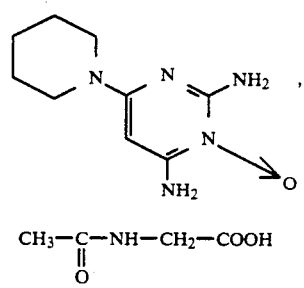

The invention also encompasses the process for preparing minoxidil aceturate, as well as its use as an active principle in dermato-cosmetic compositions, especially in hair-care compositions intended for the treatment of alopecia.

2 Claims, No Drawings

SALT OF 6-PIPERIDINO-2,4-DIAMINOPYRIMIDINE 3-OXIDE AND ACETURIC ACID, ITS PREPARATION AND ITS DERMATO-COSMETOLOGICAL APPLICATION

This application is a continuation, now abandoned, Ser. No. 07/779,152, filed Oct. 21, 1991, which is a continuation of application Ser. No. 07/410,660, filed Sep. 21, 1989, now abandoned.

The present invention relates to minoxidil aceturate, that is to say the salt obtained by salification of minoxidil, or 6-piperidino-2,4-diaminopyrimidine 3-oxide, with aceturic acid, or acetylglycine, corresponding to the formula I

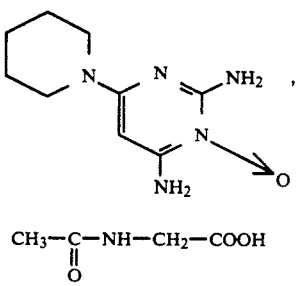

$$CH_3-C-NH-CH_2-COOH$$
$$\parallel$$
$$O$$

The subject of the present invention also encompasses the process for preparing minoxidil aceturate, as well as its use as an active principle in dermato-cosmetic compositions, especially in hair-care compositions intended for the treatment of alopecia.

Minoxidil is an antihypertensive compound well known for its activity in combating hair loss, and is used on these grounds in the treatment of alopecia. As a result of its virtual insolubility in water, it has been used to date only in solutions comprising propylene glycol and ethyl alcohol, 50 to 60% by volume as regards the latter, and which are hence irritant for topical use.

The importance of the present invention consists in that, in contrast to minoxidil, which is hence virtually insoluble in water, and to aceturic acid, which is of very low water-solubility (approximately 2.7%), minoxidil aceturate possesses a solubility of 34% w/V at 20° C., corresponding to 21.8% of active minoxidil present in the aqueous solution.

Thus, it becomes possible to prepare solutions which are either completely aqueous or which contain greatly reduced amounts of propylene glycol, the latter promoting penetration of the scalp, but henceforward lacking ethanol or any other organic solvent. All risk of skin irritation due to the presence of these solvents is thereby avoided.

Minoxidil aceturate may be readily prepared by reacting minoxidil and aceturic acid in stoichiometric amounts, in an aqueous medium or in an aliphatic alcohol such as ethanol or isopropanol. The salt formed is isolated by precipitation or crystallization. This synthesis may be carried out according to Examples 1 and 2 below.

Minoxidil aceturate is a very stable, chemically well-defined crystalline compound having a melting point in the region of 155° C.

As shown by chromatographic examination in aqueous solution, minoxidil aceturate is sufficiently capable of dissociation for the activity of the minoxidil to remain unchanged.

The present invention also relates to formulations for hair-care or pharmaceutical use containing minoxidil aceturate as active principle.

Examples 3 and 4 propose two possible formulations, without implied limitation.

EXAMPLE 1

20.9 g of minoxidil and 11.7 g of aceturic acid are suspended in 500 ml of ethanol.

The mixture is brought to reflux for 1 hour.

The hot solution is cooled to 5° C.

After filtration and drying, 29.9 g of minoxidil aceturate are recovered, corresponding to a 92% yield. Melting point: 155° C.

The IR and NMR spectra are in agreement with the structure.

EXAMPLE 2

15.2 g of aceturic acid are suspended in 150 ml of water, and 27.2 g of minoxidil are then added with stirring. The crystals dissolve rapidly.

The solution obtained is concentrated to one third of its volume, and 650 ml of isopropanol are then added with brisk stirring. Minoxidil aceturate precipitates rapidly.

The mixture is cooled to 5° C. and filtered. 37.3 g of white crystals of minoxidil aceturate are thereby recovered, corresponding to an 88% yield. Melting point: 154°–157° C.

The IR and NMR spectra are in agreement with the structure.

EXAMPLE 3

3.12 g of minoxidil aceturate are dissolved in 100 ml of distilled water.

The solution obtained, containing 2 g per 100 ml of active minoxidil, is ready for use in hair care applications.

EXAMPLE 4

4.68 g of minoxidil aceturate are dissolved in a mixture of 120 ml of distilled water and 30 ml of propylene glycol.

The solution obtained, containing the equivalent of 2 g per 100 ml of active minoxidil, is ready for use in hair care applications.

The dermato-cosmetic compositions according to the invention can assume various other forms of presentation, such as shampoos, gels, fixers or other hair-care lotions. They have, in addition, proved very effective in practice for the treatment of alopecic conditions, and have, in particular, made it possible to eliminate a number of deleterious side effects, such as irritation of the scalp or weakening of the hair through dehydration, which had been observed in the past when aqueous solutions of minoxidil were used. In addition, the improved bioavailability of the active principle according to the invention enables, with aqueous-based formulations, the concentration of available dissociated minoxidil to be lowered. Some possible problems of toxicity are thus completely solved, without a decrease in the activity in combating hair loss.

What is claimed is:

1. Minoxidil aceturate corresponding to formula I

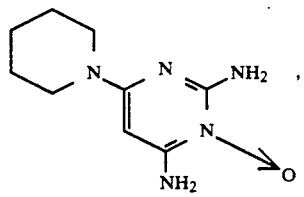
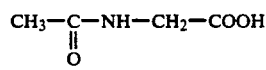
2. Dermato-cosmetic compositions, which contain minoxidil aceturate as claimed in claim 1 as active principle, dissolved in an aqueous-based vehicle.